United States Patent

Marshall

[11] 4,255,140
[45] Mar. 10, 1981

[54] APPARATUS AND METHOD FOR DENTAL IMPRESSIONS

[75] Inventor: Kenneth H. Marshall, Castlecrag, Australia

[73] Assignee: Johnson & Johnson Dental Products Company, East Windsor, N.J.

[21] Appl. No.: 45,818

[22] Filed: Jun. 6, 1979

[51] Int. Cl.³ .................. A61C 5/04; A61C 9/00
[52] U.S. Cl. ................... 433/40; 433/90; 222/575
[58] Field of Search .......... 433/40, 90, 89, 39, 433/36, 80; 222/575

[56] References Cited

U.S. PATENT DOCUMENTS

| | | | |
|---|---|---|---|
| 2,349,607 | 5/1944 | Berger | 433/40 |
| 2,452,903 | 11/1948 | Coffey | 433/80 |
| 2,648,906 | 8/1953 | Holmes | 433/39 |
| 3,143,257 | 8/1964 | Munford | 222/575 |
| 3,304,608 | 2/1967 | Frohnecke | 433/40 |
| 3,357,104 | 12/1967 | Green et al. | 433/40 |
| 3,390,458 | 7/1968 | Lytton | 433/40 |
| 3,445,935 | 5/1969 | Marshall | 433/51 |
| 3,600,810 | 8/1971 | Marshall | 433/75 |
| 3,686,754 | 8/1972 | Klondoloff | 433/40 |
| 3,722,097 | 5/1973 | Colman et al. | 433/36 |
| 4,074,436 | 2/1978 | Marshall | 433/75 |

OTHER PUBLICATIONS

"The Premach System", Premach Pty. Ltd. brochure, pp. 6-7.

Primary Examiner—Gene Mancene
Assistant Examiner—John J. Wilson

[57] ABSTRACT

Dental impressions are formed without retraction of the gingival tissue by injecting impression material from a syringe having a flexible tubular member positioned over the prepared tooth. The tubular member has a diameter corresponding to the size of the tooth and a tip contoured to the approximate shape of the gingival margin. The tubular member is initially positioned with the contoured tip extending into the gingival sulcus. As the impression material is injected around the tooth the tubular member is slowly withdrawn so that the tooth is fully covered with impression material extending completely into the gingival crevice. A full arch impression tray is then positioned within the mouth of the patient and the impression material allowed to harden.

8 Claims, 4 Drawing Figures

U.S. Patent  Mar. 10, 1981  4,255,140
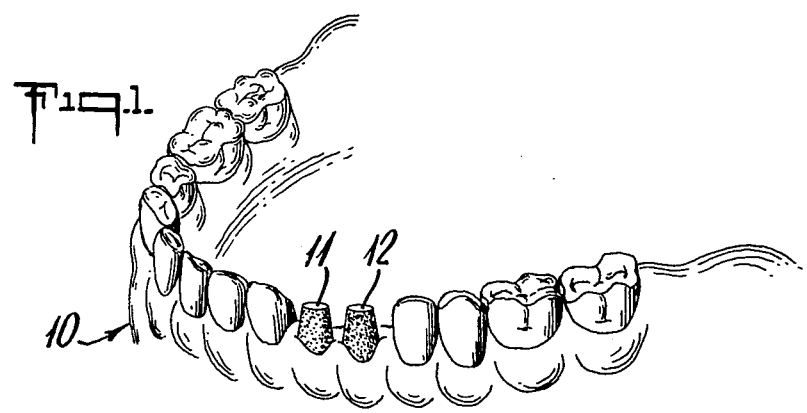
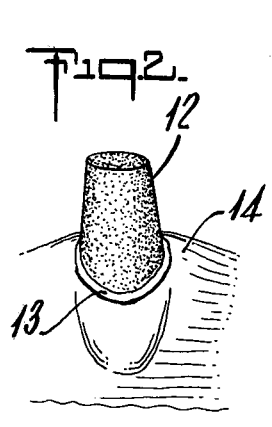
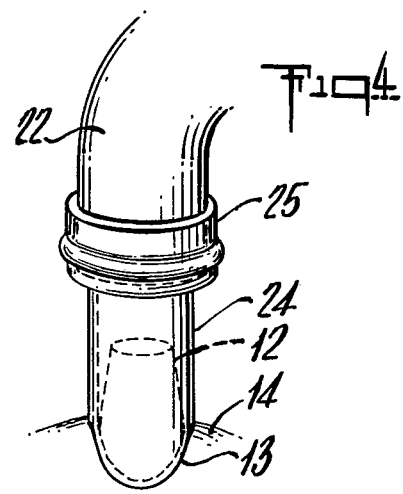
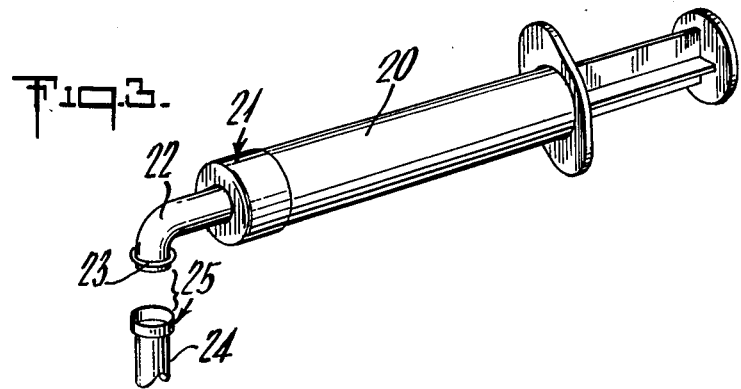

APPARATUS AND METHOD FOR DENTAL IMPRESSIONS

BACKGROUND OF THE INVENTION

This invention relates to the preparation of dental impressions of prepared teeth for fitting jacket crowns, bridgework and the like, and, more particularly, to a method and apparatus for preparing dental impressions without retraction of the gingival tissue.

In the preparation of teeth for fitting of full or partial jacket crowns, circumferential reduction of the tooth is required to compensate for the wall thickness of the crown. This reduction may be accomplished freehand, but is preferably conducted with a dental instrument such as described in U.S. Pat. Nos. 3,445,935 and 3,600,810. The use of such an instrument assures uniform reduction of the tooth below the gingival margin with slightly tapered walls. The length of the tooth is reduced freehand as required to accept the crown.

Following reduction of the tooth, it is necessary to take a dental impression of the prepared tooth and the associated teeth in that jaw in order for the dental technician to fabricate the desired crown or bridgework. In forming the dental impression, it is essential that the detail of the gingival crevice and shoulder of the prepared tooth be precisely obtained in order to assure proper fit of the crown for good functional and cosmetic effect.

It has been the general practice in the dental profession to retract the gingival tissue to provide access for the impression material into the gingival crevice. Retraction may involve the physical removal of tissue by surgical or electrosurgical means, or may be accomplished by means of retraction strings which are chemically treated and packed into the gingival crevice. Such retraction is necessarily limited to healthy tissue, and the retraction method must be carefully performed to avoid tissue damage and permanent recession of the gingiva.

Retraction is often associated with problems relating to laceration of the tissue and hemorrhage, debris left in the prepared area, irreversible tissue damage caused by prolonged contact with the chemical agent in the retraction string or by extending surgical alteration too far into the gingival crevice, and adverse physiological reactions of some patients to the chemicals of the retraction strings, particularly those associated with high blood pressure or heart disease.

It has been suggested in my earlier patent, U.S. Pat. No. 4,074,436, that the need for retraction may be eliminated by fixing an open copper tube in the impression tray at a position to enclose the prepared tooth, with the end of the tube extending into the gingival crevice and contoured to conform to the contour of the gingival margin. The tray is loaded with impression material around the open tubes and positioned firmly within the mouth of the patient. Additional impression material is then injected from a syringe into the copper tubes with sufficient pressure to force the material into the gingival crevice. After allowing the impression material to harden, the tray is carefully removed along the axis of the prepared tooth while taking precautions against bending the copper tube. While the aforedescribed copper tube method is effective to obtain detailed impressions without retraction of the gingival tissue, it has certain other disadvantages. In particular, it requires the services of a dental technician or laboratory to contour the tip of copper tube to the shape of the gingival margin and to secure the copper tube in an acrylic impression tray as described in U.S. Pat. No. 4,074,436. There is also some risk of damage to the gingival tissue during the impression procedure if the end copper tube is inserted too deeply into the gingival crevice. Moreover, the copper tube cannot be contoured as described in U.S. Pat. No. 4,074,036 until after the basic dental instrument used in the tooth reduction is prepared as described in my patent, U.S. Pat. No. 3,600,810. These and other disadvantages of the copper tube method are resolved by means of the present invention.

It is accordingly an object of the present invention to provide a method for forming impressions of a prepared tooth without retraction of the gingival tissue. It is another object of this invention to provide a method and apparatus for assuring the formation of good impressions without risk of damage to the gingival tissue. It is a further object of this invention to provide apparatus for forming impressions which can be used by the dentist without the expense or delay involved in utilizing the services of a dental laboratory. These and other objects of the present invention will be apparent from the ensuing description and claims.

SUMMARY

Impressions of prepared teeth are obtained using an apparatus comprising a dental syringe having a flexible tip contoured to approximate the contour of the gingival margin. The flexible tip is provided in a range of sizes corresponding to the range of tooth diameters found in humans, and the end of each flexible tip is contoured to approximate the contour of the gingival margin commonly associated with a tooth of that diameter.

In forming an impression of a prepared tooth, a flexible tip of an appropriate size is selected and the contour adjusted, if necessary, to conform more closely to the contour of the subgingival shoulder of the prepared tooth. The flexible tip is then attached to a syringe loaded with impression material and positioned over the tooth with the contoured end extending into the gingival crevice. Since the flexible tip is made of a relatively soft, flexible material, it is readily trimmed if necessary to conform to the contour of the shoulder of the tooth and there is no danger of damage to the gingival tissue.

With the flexible tip in position over the prepared tooth, the impression material is forced from the syringe and through the tip with sufficient pressure to force the material into the gingival crevice. As the material is observed to exude from the gingival crevice, the flexible tip is withdrawn from the tooth while impression material continues to be forced from the syringe. The result is a complete covering of the prepared tooth with impression material extending completely into the gingival cavity.

The process is repeated for each prepared tooth if more than a single restoration is involved. Following the covering of each such tooth, a full arch impression tray loaded with impression material is positioned within the mouth of the patient. The syringe injected impression material and tray material combine into one homogeneous mass. After the impression material has hardened, the tray is removed with a full impression of the jaw including the prepared teeth.

DESCRIPTION OF DRAWINGS

FIG. 1 illustrates a lower jaw of a patient with two front teeth reduced for jacket crowns.

FIG. 2 illustrates in detail one prepared tooth.

FIG. 3 illustrates a dental syringe and separated flexible tip.

FIG. 4 is a partial view of the flexible tip attached to the syringe and positioned over the tooth of FIG. 2.

DESCRIPTION OF INVENTION

Referring now to FIG. 1, there is illustrated lower jaw 10 of a human patient in which tooth 11 and tooth 12 have been reduced in preparation for a jacket crown. Reduction of the teeth is accomplished in a conventional manner and preferably in accordance with the method of U.S. Pat. No. 3,600,810 which assures uniform circumferential and subgingival reduction with slightly tapering walls. The reduced tooth is illustrated in greater detail in FIG. 2 where the gingiva in the foreground has been removed from around the tooth for clarity of illustration.

In FIG. 2, tooth 12 has been reduced to form subgingival shoulder 13 which closely follows the contour of the gingival margin 14. As illustrated, the gingival tissue in front of the tooth has been removed to reveal shoulder 13.

Referring now to FIG. 3, there is illustrated syringe barrel 20 having rigid syringe adaptor 21 attached thereto by means of screw threads or other cylindrical locking means. The adaptor may be angled up to about 90 degrees from the longitudinal axis of the syringe for convenience of use, and reduced at the distal end 22 to receive flexible tip 25. The distal end of adaptor 21 preferably provided with a circumferential surface variation such as ridge 23 illustrated in FIG. 3 to assure secure attachment of the flexible tip. Such surface variations may also comprise serrations or other tubular gripping means.

Flexible tip 25 has a proximal end sized to fit tightly over adaptor 21, and a distal end 24 sized to fit snugly over the prepared tooth. Additionally, the distal end of the flexible tip is contoured to match the contour of the gingival margin of the prepared tooth. Since the diameters of prepared teeth may vary over a range of from about 3/16 to about ½ inch, the distal end of the flexible tip is provided in a corresponding range of sizes with the inside diameter increasing in increments of 1/64 inch. The size of the proximal end of flexible tip is constant to fit one size syringe adaptor. The contour of the distal end of the flexible tip is molded to the average contour of the gingival margin of a tooth corresponding to the particular size of the tip. While such average contours are only an approximation, the flexibility of the tip allows some conformation to variations between individual teeth, and the tip can be easily trimmed with curved scissors if additional adaptation is required.

FIG. 4 illustrates the flexible tip attached to the end of the syringe and positioned over the prepared tooth ready for injection of the impression material. The flexible tip extends into the gingival crevice so that the impression material is forced into the subgingival area and around the shoulder of the tooth to obtain precise detail of this critical area. In forming the impression, an appropriately sized and contoured flexible tip is selected and attached to the syringe, and the syringe is loaded with impression material. The flexible tip is then positioned over the tooth as illustrated in FIG. 4 and the impression material discharged into the gingival crevice. As the gingival crevice fills and excess material exudes from around the flexible tip, the tip is withdrawn from the tooth while additional impression material is discharged. As the flexible tip is fully withdrawn, the tooth is left with a complete covering of impression material, extending into the subgingival area of the tooth.

The impression process is repeated with any other prepared teeth in the jaw. To avoid delay, individual impression syringes are loaded with flexible tips attached for each tooth to be restored before the impression procedure is initiated. After each prepared tooth has been covered with injected impression material, a full arch impression tray loaded with additional impression material is positioned over the teeth and the impression is allowed to harden. Upon removal of the tray, there is obtained a complete negative of the jaw including detailed impressions of the teeth under restoration from which jacket crowns, bridges, and the like may be prepared in a conventional manner.

The flexible impression tips may be fabricated of any resilient but relatively inelastic material such as Teflon, polyethylene, polypropylene, and the like. The tips are preferably molded in the desired sizes and tip contours and may be discarded after use. The syringe and syringe extension are fabricated of rigid plastic and may be either reusable or disposable depending on construction and cost.

What is claimed is:

1. Apparatus for forming a dental impression of a reduced tooth comprising
   a dental impression syringe,
   a rigid adaptor removably secured to said dental syringe, and
   a flexible tubular member having a proximal end removably secured to said adaptor and a distal end adapted to fit snugly over the reduced tooth, the tip of said distal end being contoured to the general shape of the gingival margin of said tooth.

2. The appartaus of claim 1 wherein the proximal end of said tubular member is secured over the tip of the adaptor inserted therein.

3. The apparatus of claim 2 wherein the tip of said adaptor includes means for gripping said flexible tubular member when said adaptor is inserted into said tubular member.

4. The apparatus of claim 3 wherein said gripping means comprises a ridge circumscribing the tip of said adaptor.

5. The apparatus of claim 1 wherein the inside diameter of the distal end of said tubular member is from about 3/16 to ½ inch.

6. The apparatus of claim 1 wherein the tip of the adaptor is angled from 0 to 90 degrees from the longitudinal axis of the syringe.

7. A method of forming an impression of a reduced tooth without retraction of the gingival tissue which comprises
   providing a flexible tubular member having an inside diameter substantially conforming to the diameter of the reduced tooth, and a tip contoured to the general shape of the gingival margin of said tooth;
   positioning said tubular member over said tooth with said contoured end extending into the gingival crevice of said tooth;
   forcing impression material through said tubular element and into said gingival crevice until said material exudes from between the tip of said tubular member and said gingival crevice;

withdrawing said tubular member from said tooth while simultaneously forcing additional impression material through said tubular member until said tubular member is completely removed from said tooth and said tooth is completely covered with impression material extending into the gingival crevice thereof;

inserting a full arch impression tray loaded with impression material over the reduced tooth and adjacent teeth;

allowing said impression material to harden, and removing said impression tray;

whereby a detailed impression of the reduced tooth including the subgingival area is obtained without retraction in a full arch impression.

8. The method of claim 7 wherein the tip of the flexible tubular element is trimmed to conform specifically to the contour of a subgingival shoulder of said reduced tooth.

* * * * *